US00PP25293P3

(12) United States Plant Patent
Hernandez

(10) Patent No.: US PP25,293 P3
(45) Date of Patent: Feb. 17, 2015

(54) *TULBAGHIA* PLANT NAMED 'HINETUL1'

(50) Latin Name: *Tulbaghia violacea*
Varietal Denomination: Hinetul1

(71) Applicant: Hines Growers, Inc., Fallbrook, CA (US)

(72) Inventor: David Hernandez, Orange, CA (US)

(73) Assignee: Hines Growers, Inc., Fallbrook, CA (US)

( * ) Notice: Subject to any disclaimer, the term of this patent is extended or adjusted under 35 U.S.C. 154(b) by 0 days.

(21) Appl. No.: 13/986,204

(22) Filed: Apr. 11, 2013

(65) Prior Publication Data

US 2014/0310840 P1 Oct. 16, 2014

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — June Hwu
*Assistant Examiner* — Keith Robinson
(74) *Attorney, Agent, or Firm* — Barbara Campbell; Cochran Freund & Young LLC

(57) ABSTRACT

A *Tulbaghia* plant particularly distinguished by purple inflorescences and green, yellow-green, and white variegated foliage with purple margins, is disclosed.

2 Drawing Sheets

Genus and species: *Tulbaghia violacea.*
Variety denomination: 'Hinetul1'.

BACKGROUND OF THE NEW PLANT

The present invention comprises a new and distinct variety of *Tulbaghia*, botanically known as *Tulbaghia violacea*, and hereinafter referred to by the variety name 'Hinetul1'. The new variety originated as a whole plant mutation in an unnamed and unpatented bed of *Tulbaghia violacea* in June 2002 in a nursery in Irvine, Calif.

The new plant was first asexually propagated in Irvine, Calif. in April 2003 and has been asexually reproduced by divisions for approximately 9 years in Irvine, Calif. The present invention has been found to retain its distinctive characteristics through successive asexual propagations by divisions.

'Hinetul1' has not been made publicly available or sold more than one year prior to the filing of this application.

SUMMARY

The following are the most outstanding and distinguishing characteristics of the new variety when grown under normal horticultural practices in Irvine, Calif.

1. Large, purple inflorescences; and
2. Green, yellow-green, and white variegated foliage with purple margins.

DESCRIPTION OF THE PHOTOGRAPHS

This new *Tulbaghia* plant is illustrated by the accompanying photographs which show the overall plant habit, foliage and inflorescence of the plant. The colors are as true as can be reasonably obtained by conventional photographic procedures. The photographs are of plants grown outdoors in Irvine, Calif. in 2012.

DESCRIPTION OF THE NEW VARIETY

Figure 1:
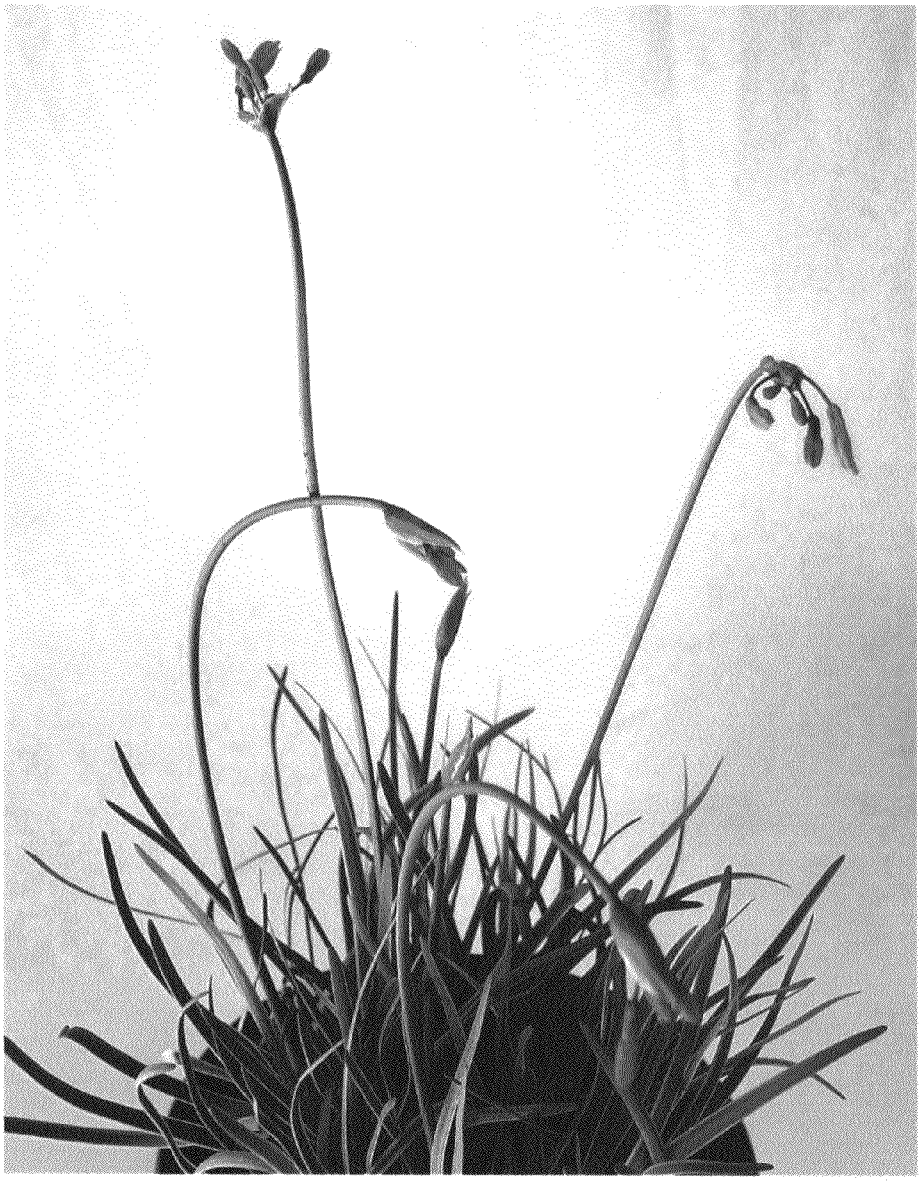
FIG. 1 shows a the whole plant, including the habit, foliage and inflorescence.
Figure 2:
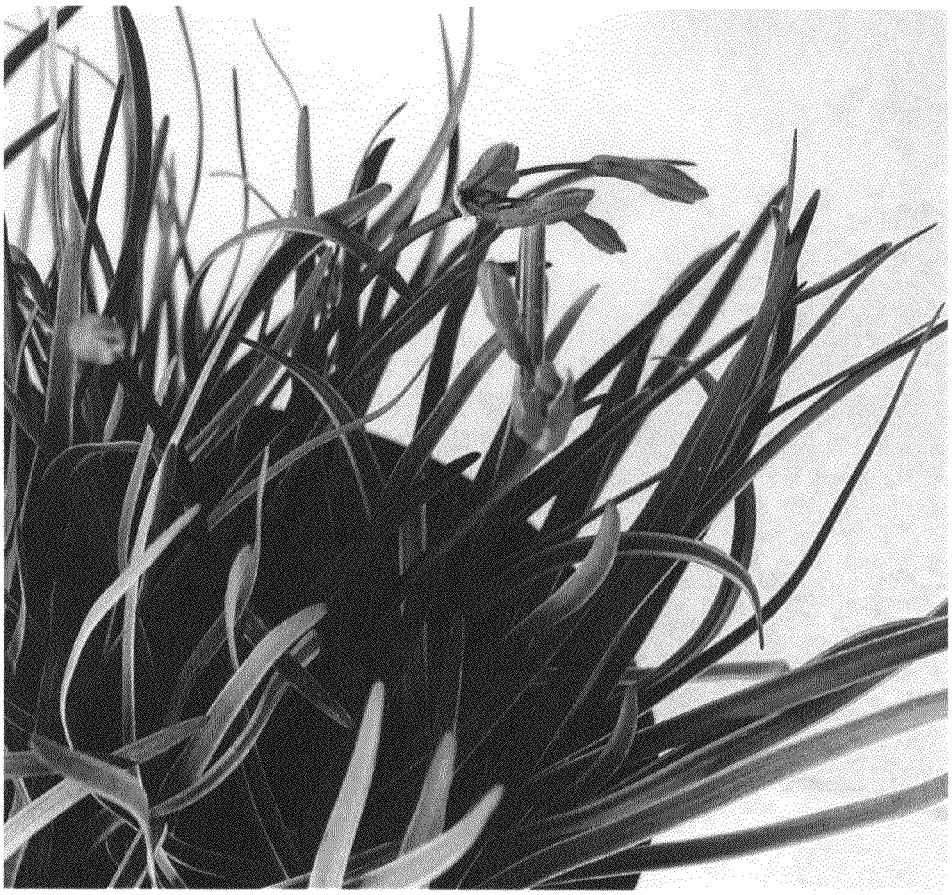
FIG. 2 shows a close-up of the foliage and inflorescence.

The following detailed descriptions set forth the distinctive characteristics of 'Hinetul1'. The data which defines these characteristics were collected from asexual reproductions carried out in Rainbow, Calif. The plant history was taken in October 2012 on plants grown outdoors in Rainbow, Calif. Color references were taken under natural light and are to The R.H.S. Colour Chart of The Royal Horticultural Society of London (R.H.S.), third edition. Texture descriptions were taken using a dissecting microscope.

Classification:
- *Family.*—Amaryllidaceae.
- *Botanical name.*—*Tulbaghia violacea.*
- *Denomination.*—'Hinetul1'.

Parentage:
- *Mutation parent.*—*Tulbaghia violacea* (unnamed and unpatented).

Plant:
- *Propagation type.*—Divisions.
- *Plant height (excluding inflorescence).*—25.4 cm to 27.94 cm.
- *Habit.*—Upright growing with gently arching leaves growing from a central clump.
- *Plant spread.*—12.0 inches to 18.0 inches.
- *Blooming period.*—Year round in warmer climates, but natural blooming season is spring and summer.
- *Hardiness.*—Frost damage occurs when temperatures reach 20-25° F.
- *Fragrance.*—Flowers and stems have an onion or garlic odor.
- *Plant disease/insect resistance/susceptibility.*—None observed.
- *Seed.*—None observed.

*Market use*.—For use in herb gardens, perennial gardens, mixed gardens, dry/rock gardens.

Foliage:

*Length*.—17.78 cm to 30.48 cm.

*Width*.—6.0 cm.

*Color*.—Upper surface: Repetitive and random stripes of RHS 137C, RHS 138D, and RHS 145D with RHS 74D on the margins. Lower surface: Repetitive and random stripes of RHS 145D, RHS 138C, and RHS 137B with RHS 75A on the margins.

*Texture* (*both upper and lower surfaces*).—Smooth.

*Shape*.—Linear.

*Apex*.—Rounded.

*Base*.—Sheathed.

*Margin*.—Entire.

Inflorescence:

*Height*.—33.02 cm to 43.18 cm.

*Umbel shape*.—Star shaped.

*Umbel width*.—2.54 cm to 5.08 cm.

*Individual flower width*.—1.59 cm.

*Individual flower length*.—1.4 cm.

*Individual flower shape*.—Oblong.

*Petals*.—Upper surface: RHS 81D. Lower surface: RHS 80C.

*Scape* (*flowering stalk*).—Length: 55.88 cm. Diameter: 4.0 mm. Color: RHS 90A.

COMPARISON WITH PARENTAL AND COMMERCIAL VARIETIES

'Hinetul1' differs from the commercial comparison 'Pertaylor' (U.S. Plant Pat. No. 9,019) in that 'Hinetul1' has purple inflorescences and green, yellow-green, and white variegated foliage with purple margins, while 'Pertaylor' has nearly white inflorescences and does not have variegated foliage.

'Hinetul1' differs from the parental bed of *Tulbaghia violacea* from which it arose in that 'Hinetul1' has green, yellow-green, and white variegated foliage with purple margins, while the parental bed of *Tulbaghia violacea* from which it arose has green, yellow-green, and white variegated foliage.

I claim:

1. A new and distinct variety of *Tulbaghia* plant as shown and described herein.

* * * * *